(12) United States Patent  
Harandi

(10) Patent No.: US 11,103,844 B2  
(45) Date of Patent: Aug. 31, 2021

(54) ADVANCED STEAM CRACKING

(71) Applicant: ExxonMobil Research and Engineering Company, Annandale, NJ (US)

(72) Inventor: Mohsen N. Harandi, New Hope, PA (US)

(73) Assignee: ExxonMobil Research and Engineering Company, Annandale, NJ (US)

(*) Notice: Subject to any disclaimer, the term of this patent is extended or adjusted under 35 U.S.C. 154(b) by 218 days.

(21) Appl. No.: 16/453,339

(22) Filed: Jun. 26, 2019

(65) Prior Publication Data

US 2020/0047142 A1 Feb. 13, 2020

Related U.S. Application Data

(60) Provisional application No. 62/716,672, filed on Aug. 9, 2018.

(51) Int. Cl.
*B01J 8/18* (2006.01)
*B01J 8/22* (2006.01)
(Continued)

(52) U.S. Cl.
CPC .............. *B01J 8/1836* (2013.01); *B01J 8/22* (2013.01); *C10G 9/16* (2013.01); *C10G 9/32* (2013.01); *C01B 2203/148* (2013.01)

(58) Field of Classification Search
CPC .. B01J 8/1836; B01J 8/22; B01J 2208/00132; B01J 2208/00309; B01J 19/0013;
(Continued)

(56) References Cited

U.S. PATENT DOCUMENTS

| 4,990,712 A | 2/1991 | Harandi et al. |
| 6,190,533 B1 | 2/2001 | Bradow et al. |

(Continued)

FOREIGN PATENT DOCUMENTS

| WO | 2017142739 A1 | 8/2017 |
| WO | 2017173519 A1 | 10/2017 |

OTHER PUBLICATIONS

Grace, Multiphase Catalytic Reactors: Theory, Design, Manufacturing and Applications, First Edition (Year: 2016).*

(Continued)

*Primary Examiner* — Randy Boyer  
*Assistant Examiner* — Juan C Valencia  
(74) *Attorney, Agent, or Firm* — Kristina Okafor; Priya G. Prasad; Robert A. Migliorini

(57) ABSTRACT

A process and system that use the heat produced in the generation of Syngas to provide heat to an endothermic reaction zone are disclosed. A method for providing heat to an endothermic reaction may comprise producing Syngas in a reforming reactor. The method may further comprise recovering heat from the producing the Syngas to heat an endothermic reaction stream in a heat transfer zone. The method may further comprise allowing reactants in the endothermic reaction stream to react to form an endothermic reaction product stream. The method may further comprise withdrawing the endothermic reaction product stream from the heat transfer zone.

15 Claims, 3 Drawing Sheets

(51) Int. Cl.
*C10G 9/16* (2006.01)
*C10G 9/32* (2006.01)

(58) Field of Classification Search
CPC .. B01J 19/002; B01J 8/34; C10G 9/16; C10G 9/32; C10G 2/344; C10G 35/00; C10G 9/36; C01B 2203/148; C01B 2203/0872; C01B 2203/0233; C01B 2203/0244; C01B 2203/0261; C01B 3/44; C01B 3/34; Y02P 20/50; C07C 29/1518; C07C 2/76; C07C 5/333; F28D 2021/0075
See application file for complete search history.

(56) References Cited

U.S. PATENT DOCUMENTS

| | | | | |
|---|---|---|---|---|
| 2004/0014826 | A1* | 1/2004 | Wang | B01J 19/2485 423/651 |
| 2005/0187415 | A1* | 8/2005 | Lawson | C10J 3/00 585/324 |
| 2006/0143980 | A1* | 7/2006 | Rapier | C01B 3/386 48/61 |
| 2012/0006723 | A1 | 1/2012 | Davis et al. | |
| 2016/0362613 | A1 | 12/2016 | Cunningham et al. | |
| 2017/0233667 | A1 | 8/2017 | Harandi et al. | |
| 2017/0320730 | A1* | 11/2017 | Mamedov | C01B 3/382 |
| 2018/0194701 | A1* | 7/2018 | Hong | C07C 2/46 |

OTHER PUBLICATIONS

International Search Report and Written Opinion issued in related Application No. PCT/US2019/039242, dated Sep. 18, 2019 (13 pages).

* cited by examiner

ADVANCED STEAM CRACKING

CROSS-REFERENCE TO RELATED APPLICATIONS

This application claims the benefit of U.S. Provisional Application No. 62/716,672, filed on Aug. 9, 2018, the entire contents of which are incorporated herein by reference.

FIELD

This application relates to steam cracking and other endothermic chemical reactions, and, more particularly, embodiments relate to a process and system that use the heat produced in the generation of Syngas to provide heat to an endothermic reaction zone.

BACKGROUND

Thermal cracking of hydrocarbons is a petrochemical process that is widely used to produce olefins such as ethylene, propylene, butylenes, butadiene, and BTX (e.g., mixtures of benzene, toluene, and xylenes). Steam cracking is one technique that produces olefins by thermal cracking of hydrocarbon feedstocks in the presence of steam at elevated temperatures. Typically, the feedstock for steam cracking may include gaseous or liquid hydrocarbons, such as naphtha, vacuum gas oils, and natural gas liquids (e.g., liquefied petroleum gas, condensate, ethane, propane, butane, etc.). In conventional steam cracking, the hydrocarbon feedstock is heated in a steam-cracking furnace to cracking temperatures, which may range from 1,450° F. (790° C.) to 1,650° F. (900° C.) or even higher. At these high temperatures, cracking reactions occur that break down the saturated hydrocarbons into smaller hydrocarbons (e.g., conversion of ethane to ethylene). These cracking reactions typically occur in the absence of a catalyst. The resulting products, including olefins, leave the steam-cracking furnace for further downstream processing.

In the steam-cracking furnace, the hydrocarbon feedstocks may be converted to more valuable products. Steam cracking furnaces can use a variety of fuels, which may range from natural gas to crude oil. There may be drawbacks to the use of conventional steam-cracking furnaces. For example, steam-cracking furnaces may have a large footprint and, for safety reasons, are often required to be placed at specified distances from other processing equipment. In addition, steam-cracking furnaces also can be highly energy intensive, for example, due to the high temperatures required for cracking. The steam-cracking furnace can result in excessive fuel usage, as well as undesired production of nitrogen oxides ("$NO_x$") and carbon dioxide. Since $NO_x$ and carbon dioxide emissions are often regulated, it is desired to reduce their emissions. Even further, steam cracking also can result in formation of coke on the reactor walls, which can degrade the efficiency of the process, resulting in frequent shutdowns for de-coking. The coking can be a result of high and non-uniform temperatures generated in the steam-cracking furnace. Additionally, due to low heat transfer coefficients in the steam-cracking furnace, the reactor tubes can have an excessive surface area to provide sufficient surface area for heat transfer. These heat transfer inefficiencies can also lead to longer residence times which can result in lower yields. Departure from isothermal conditions due to non-uniform temperatures may also contribute to lower than desired yields.

SUMMARY

Disclosed herein is an example method for providing heat to an endothermic reaction, including producing Syngas in a reforming reactor. The method may further include recovering heat from the producing of the Syngas to heat an endothermic reaction stream in a heat transfer zone. The method may further include allowing reactants in the endothermic reaction stream to react to form an endothermic reaction product stream. The method may further include withdrawing the endothermic reaction product stream from the heat transfer zone.

Further disclosed herein is another example method for reducing flue gas emissions from furnaces of endothermic reactions, including supplying an endothermic reaction stream to an endothermic reaction zone; recovering heat from a Syngas in the endothermic reaction zone to heat the endothermic reaction stream; and allowing reactants in the endothermic reaction stream to react to form an endothermic reaction product stream.

Further disclosed herein is an example system including a reforming reactor operable to convert a hydrocarbon-containing feed into a Syngas; a heat transfer zone operable to recover heat from conversion of the hydrocarbon-containing feed; and an endothermic reaction zone disposed in the heat transfer zone.

BRIEF DESCRIPTION OF THE DRAWINGS

These drawings illustrate certain aspects of the present invention and should not be used to limit or define the invention.

DETAILED DESCRIPTION

This application relates to steam cracking and other endothermic chemical reactions, and, more particularly, embodiments relate to a process and system that use the heat produced in the generation of Syngas to provide heat to an endothermic reaction zone. While the methods and systems disclose herein may be suitable to provide heat to any of a variety of endothermic chemical reactions, they may be particularly suitable for steam cracking.

There may be several potential advantages to the methods and systems disclosed herein, only some of which may be alluded to in the present disclosure. One of the many potential advantages of the methods and systems is that inefficiencies from use of furnaces for supply of heat to endothermic reactions may be addressed. The production of Syngas is highly exothermic, for example, in authothermal reforming. Accordingly, Syngas production typically may produce a gas at relatively high pressures that can enable more uniform heat transfer with an endothermic reaction feed, such as a steam cracker feed, than full combustion in furnace fire-boxes. By elimination of the furnace, problems associated with the furnace may also be eliminated. Such problems may include inefficient fuel usage, NO$_x$ production, CO$_2$ emissions, large footprint, remote placement, and excessive coking, among others. In addition, non-uniform temperatures and hot spots from full combustion may be reduced or potentially even eliminated. In some embodiments, the heat from Syngas production may be used to heat a fluidized bed, whether inert or catalytic, in which tubes carrying the endothermic reaction may be disposed. The fluidized bed may maintain a relatively constant temperature so that the heat transfer zone may be considered isothermal. By maintaining isothermal conditions in the heat transfer zone, tube areas may be minimized. In addition, the high heat transfer coefficient of an optimized (e.g., optimum gas velocity, particle size distribution and/or particle density) fluidized bed can also minimize residence time in the endothermic reaction zone, thus increasing yield.

Figure 1:
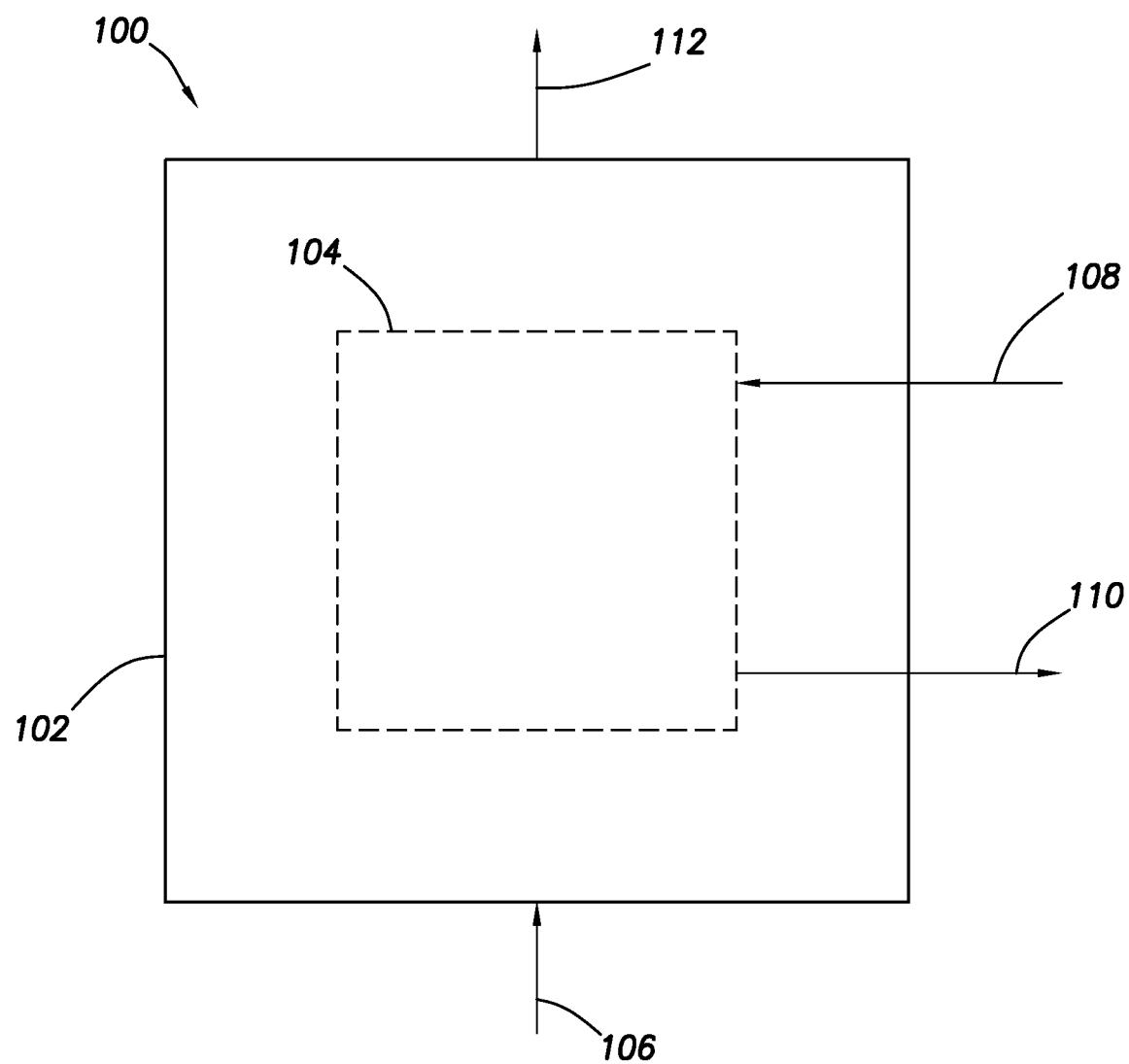
FIG. 1 is a schematic diagram illustrating an embodiment for heating an endothermic reaction feed stream.

FIG. 1 illustrates an embodiment of an endothermic reaction system 100. As illustrated, the endothermic reaction system 100 may include a heat transfer zone 102 and an endothermic reaction zone 104. In the illustrated embodiment, the endothermic reaction zone 104 may be disposed in the heat transfer zone 102. As will be discussed in more detail below, in certain embodiments, a Syngas stream 106 may be provided to the heat transfer zone 102 and used to provide heat to the endothermic reaction zone 104. As illustrated, an endothermic reaction feed stream 108 may be supplied to the endothermic reaction zone 104 and heated by the Syngas stream 106 such that the endothermic reaction occurs. An endothermic reaction product stream 110 may be withdrawn from the endothermic reaction zone.

The Syngas stream 106 may include synthesis gas, commonly referred to as "Syngas." Syngas typically may include a mixture of carbon monoxide, carbon dioxide and hydrogen. Syngas may be produced from a variety of hydrocarbon-containing feeds. Examples of suitable hydrocarbon-containing feeds may include natural gas (mainly methane, but natural gas composition can vary depending on location and source), naphtha, refinery off-gas, liquefied petroleum gas (LPG), gas oil, vacuum residuals, shale oils, asphalts, various types of fuel oils, coal based/lignin deposits, hydrocarbon containing process recycle streams and biomass derived gas, among others. Syngas may be an intermediate in the production of a more valuable product, including, but not limited to, methanol, gasoline, dimethyl ether, distillates (e.g., jet fuel, kerosene, diesel fuel), and BTX (e.g., mixtures of benzene, toulene, and xylenes). The relative concentrations of the components in the Syngas may vary based on the production process and raw materials, among other factors, but a typical Syngas may include carbon monoxide in amount of about 15% to about 50% by volume of the Syngas, hydrogen in an amount of about 10% to about 60% by volume of the Syngas, and carbon dioxide in an amount of about 1% to about 20% by volume of the Syngas. In some embodiments, the Syngas may include carbon monoxide in amount of about 30% to about 50% by volume of the Syngas, hydrogen in an amount of about 25% to about 30% by volume of the Syngas, and carbon dioxide in an amount of about 5% to about 15% by volume of the Syngas. Additional components may also be present in the Syngas, including, but not limited to methane, water vapor, and hydrogen sulfide, among others.

Any suitable technique may be used for production of the Syngas stream 106 so long as the Syngas stream 106 may be supplied at relatively high temperatures. In some embodiments, Syngas may be supplied by generation within the endothermic reaction system 100. In some embodiments, the Syngas stream 106 may at a temperature ranging from about 1400° F. (760° C.) to about 2500° F. (1370° C.). For example, the Syngas stream 106 may be at a temperature ranging from about 1800° F. (980° C.) to about 2200° F. (1200° C.). In addition, the Syngas stream 106 may also be at elevated pressures. For example, the Syngas stream 106 may be at a pressure ranging from about 5 pounds per square inch ("psi") (35 kilopascals ("KPa")) to about 900 psi (6,200 KPa) and, more particularly, from about 30 psi (205 KPa) to about 350 psi (2,410 KPa). However, the scope of the disclosure is not limited to these values of temperature and pressure for the Syngas stream 106. Rather, the Syngas stream 106 may have any suitable temperature and pressure as desired for a particular application.

Suitable techniques for production of the Syngas stream 106 may include, but are not limited to, reaction of the hydrocarbon-containing feed with steam, carbon dioxide, and/or water. The particular process for generation of the Syngas stream 106 may depend on a variety of factors, including, but not limited to, the amount of heat generated, feedstock availability, and/or desired mole ratio of hydrogen to carbon dioxide in Syngas stream 106 for subsequent processing. Examples of suitable processes may include, but are not limited to, partial oxidation of hydrocarbons, steam reforming, gas heated reforming, microchannel reforming, plasma reforming, autothermal reforming ("ATR"), and any combination thereof. One of ordinary skill in the art, with the benefit of this disclosure, should be able to select an appropriate process for providing heat to the endothermic reaction.

As illustrated, the Syngas stream 106 may be provided to the heat transfer zone 102 In some embodiments, providing the Syngas stream 106 to the heat transfer zone 102 may include directing the Syngas stream 106 from a reforming reactor (e.g., reforming reactor 204 on FIG. 2) to the heat transfer zone 102. In other embodiments, providing the Syngas stream 106 to the heat transfer zone 102 may include producing the Syngas stream 106 in the heat transfer zone 102 by appropriate reaction. In the heat transfer zone 102, the Syngas stream 106 may exchange heat with the endothermic reaction zone 104. For example, the Syngas stream 106 may heat the endothermic reaction feed stream 108 in the endothermic reaction zone 104. Any suitable technique may be used for heat transfer. In some embodiments, the Syngas stream 106 may transfer heat to the endothermic reaction zone 104 directly or indirectly. In some embodiments, the Syngas stream 106 may heat tubes (e.g., tubes 212 on FIG. 2) carrying the endothermic reaction feed stream 108 in the endothermic reaction zone 104. In some embodiments, the heat transfer zone 102 may contain a fluidized bed (e.g., fluidized bed 300 on FIG. 3). The Syngas stream 106 may heat the fluidized bed, which in turn transfers heat to the endothermic reaction zone 104. The fluidized bed may be catalytic or non-catalytic as desired for a particular application. For example, a fluidized bed that is catalytic may be used to catalyze reaction of the Syngas stream 106 to desirable products in the heat transfer zone 102 while also heating the endothermic reaction zone 104. Outlet stream 112 may be withdrawn from heat transfer zone 102. In some embodiments, the outlet stream 112 may include the Syngas from Syngas stream 106 that may be withdrawn for further processing. In other embodiments, the outlet stream 112 may include Syngas conversion products, for example, where a catalytic fluidized bed is used to convert the Syngas to products in the heat transfer zone 102.

With continued reference to FIG. 1, the endothermic reaction feed stream 108 may be supplied to the endothermic reaction zone 104. In the endothermic reaction zone 104, the endothermic reaction feed stream 108 may be heated, for example, by the Syngas stream 106, to a reaction temperature and allowed to react. The endothermic reaction feed stream 108 may be supplied to the endothermic reaction zone 104 at any suitable temperature and pressure. Suitable temperatures and pressures may include, but are not limited to, a temperature ranging from about 700° F. (370° C.) to about 1,350° F. (730° C.) and a pressure ranging from about 10 psi (70 KPa) to about 300 psi (2,070 KPa). For the embodiments with an ethane steam cracking reaction, the endothermic reaction feed stream 108 may be supplied, for example, at a temperature ranging from about 800° F. (430° C.) to about 1,300° F. (705° C.) and a pressure ranging from about 15 psi (100 KPa) to about 300 psi (2,070 KPa). However, the scope of the disclosure is not limited to these values of temperature and pressure for the endothermic reaction feed stream 108. Rather, the endothermic reaction feed stream 108 may have any suitable temperature and pressure as desired for a particular application. In some embodiments, the endothermic reaction feed stream 108 may be preheated, for example, prior to supply to the endothermic reaction zone 104. While not illustrated, the production of the Syngas stream 106 may also be used to preheat the endothermic reaction feed stream 108, for example, by cross exchange of the Syngas stream 106 and the endothermic reaction feed stream 108. In some embodiments, the endothermic reaction feed stream 108 may be preheated to within about 300° F. (150° C.) of the reaction temperature in the endothermic reaction zone 104. The endothermic reaction feed stream 108 may be heated in the endothermic reaction zone to any suitable temperature, depending, for example, on the particular endothermic reaction. In some embodiments, the endothermic reaction feed stream 108 may be heated in the endothermic reaction zone 104 to a suitable reaction temperature, for example, a temperature ranging from about 900° F. (480° C.) to about 1750° F. (950° C.) and a pressure ranging from about 1 psi (70 KPa) to about 150 psi (2,070 KPa). However, the scope of the disclosure is not limited to these values of temperature and pressure for the endothermic reaction zone 104. Rather, the endothermic reaction zone 104 may have any suitable temperature and pressure as desired for a particular application.

The endothermic reaction feed stream 108 may include feeds for any of a variety of endothermic reactions that may be heated by the Syngas stream 106. Non-limiting examples of suitable endothermic reactions may include, but are not limited to, naphtha reforming, paraffin dehydrogenation, steam cracking, and LPG conversion to BTX. In naphtha reforming, an endothermic reaction feed stream 108 including naphtha may be reacted in the endothermic reaction zone 104 to produce higher octane liquid products, commonly referred to as "reformates." For example, linear hydrocarbons may be converted into higher octane branched alkanes. In some embodiments, naphtha reforming may be performed in the endothermic reaction zone 104 at a reaction temperature ranging from about 900° F. (480° C.) to about 1100° F. (590° C.). Naphtha reforming may be used, in some embodiments, with a catalytic fluidized bed in the heat transfer zone 102, as previously described. The catalytic fluidized bed may operate at temperatures ranging from 950° F. (510° C.) to about 1150° F. (620° C.) in the conversion of the Syngas stream 106 to products, such as olefins. In paraffin dehydrogenation, an endothermic reaction feed stream 108 including alkanes may be reacted in the endothermic reaction zone 104 to produce olefins. For example, ethane may be converted to ethylene and propane may be converted to propylene. In some embodiments, paraffin dehydrogenation may be performed in the endothermic reaction zone 104 at a reaction temperature ranging from about 950° F. (510° C.) to about 1200° F. (650° C.). In steam cracking, an endothermic reaction feed stream 108 including hydrocarbons and steam may be reacted in the endothermic reaction zone 104 to produce olefins. For example, naphtha, natural gas liquids, or vacuum gas oils may be reacted with steam to produce olefins. In some embodiments, steam cracking may be performed in the endothermic reaction zone 104 at a reaction temperature, which may range from 1300° F. (700° C.) to 1750° F. (950° C.). In LPG conversion to BTX, an endothermic reaction feed stream 108 including LPG may be reacted in the endothermic reaction zone 104 to produce BTX. Suitable endothermic reactions may include, but are not limited to, the CYCLAR™ process or M-Forming reactions that aromatize LGP using metal-containing zeolites. n some embodiments, the LPG conversion to BTX may be performed in the endothermic reaction zone 104 at a reaction temperature ranging from about 950° F. (510° C.) to about 1250° F. (680° C.) and, alternatively, from about 950° F. (510° C.) to about 1100° F. (590° C.)

Figure 2:
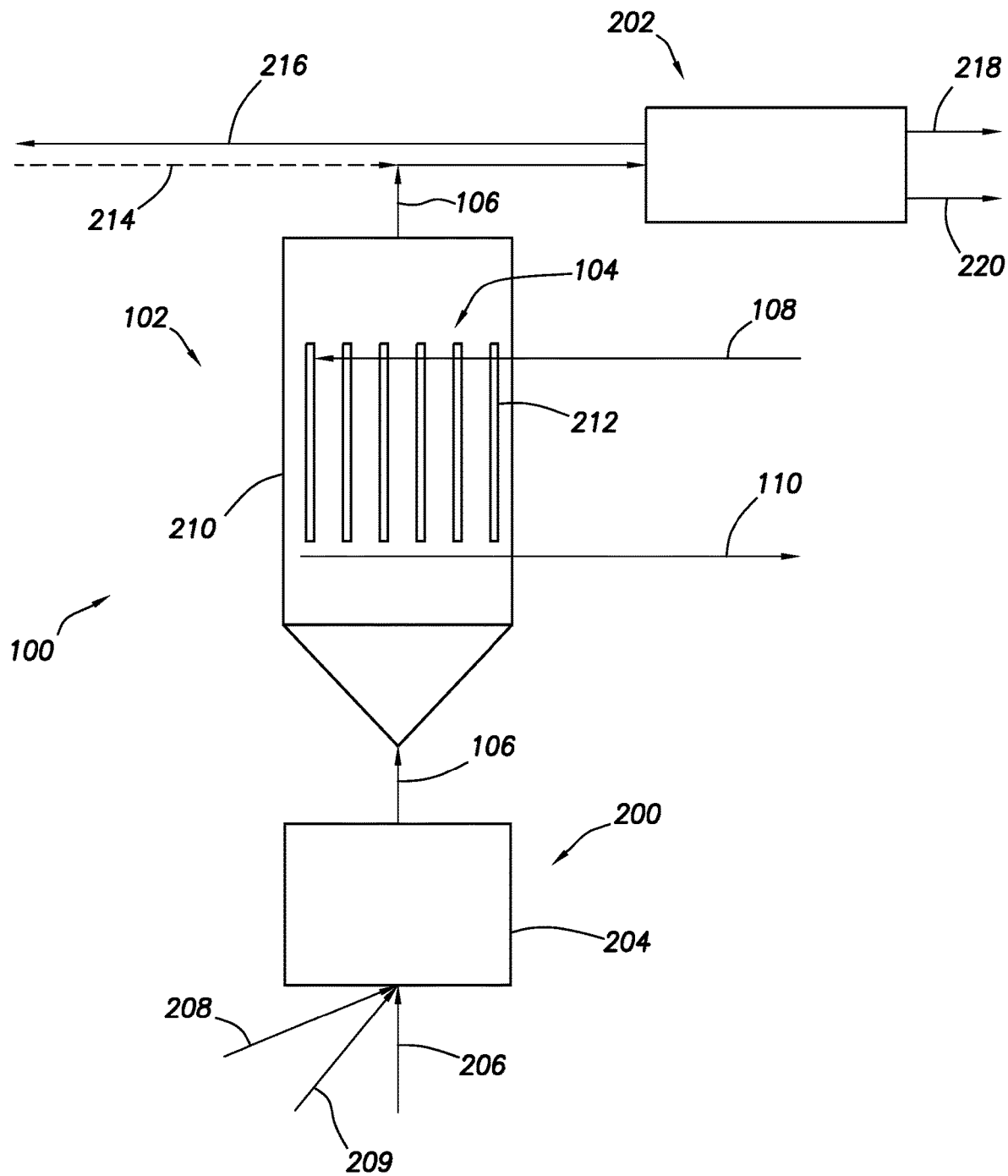
FIG. 2 is a schematic diagram illustrating another embodiment for heating an endothermic reaction feed stream.

FIG. 2 illustrates another embodiment of an endothermic reaction system 100. As illustrated, the endothermic reaction system 100 may include a gasification unit 200, a heat transfer zone 102, and a Syngas conversion unit 202. In the illustrated embodiment, an endothermic reaction zone 104 may be disposed in the heat transfer zone 102. In certain embodiments, Syngas may be produced in gasification unit 200 with a Syngas stream 106 being supplied from the gasification unit 200 to the heat transfer zone 102. In the heat transfer zone 102, the Syngas stream 106 may be used to supply heat to the endothermic reaction zone 104. An endothermic reaction feed stream 108 may be heated in the endothermic reaction zone 104 to a reaction temperature. An endothermic reaction product stream 110 may be withdrawn from the endothermic reaction zone 104. After heat transfer zone 102, Syngas stream 106 may be fed to Syngas conversion unit 202 for conversion to more valuable products.

Gasification unit 200 may include any suitable process for production of Syngas. As previously described, examples of suitable processes may include, but are not limited to, partial oxidation of hydrocarbons, steam reforming, gas heated reforming, microchannel reforming, plasma reforming, ATR, and any combination thereof. In the illustrated embodiment, gasification unit 200 may include a reforming reactor 204. In some embodiments, the reforming reactor 204 may be in the form of an ATR reactor. In ATR, a hydrocarbon-containing feed (e.g., natural gas) may be combined with oxygen in the reforming reactor 204 where exothermic reactions occur. In the illustrated embodiment, a hydrocarbon-containing feed stream 206 and an oxygen stream 208 may be introduced into the reforming reactor 204. Steam may also be added to the reforming reactor 204. As illustrated, a steam stream 209 may be introduced into the reforming reactor. In ATR of natural gas, for example, steam may be added to reduce or eliminate soot formation, to cool select components of the burner within the reforming reactor 204, and/or to reduce methane content of the generated Syngas. In the illustrated embodiment, for ATR, the reforming reactor may have any suitable steam:carbon ratio, including, but not limited to, a steam:carbon ratio ranging from 0.4 to 2.0. Suitable oxygen:carbon ratios may range, for example, from 0.4 to 0.8. However, the scope of the disclosure is not limited to these ratios for the reforming reactor 204. Rather, the reforming reactor 204 may have any steam:carbon ratio and oxygen:carbon ratio as desired for a particular application.

In some embodiments, the reforming reactor 204 may include a reforming catalyst. Examples of suitable reforming catalyst may include at least one transition element selected from the group consisting of Ni, Co, Cr, Ce, La, Pd, Pt, Ru, Rh, Ir, Pt, Os, and Fe. In some embodiments, the reforming catalyst further includes at least one metal selected from the group consisting of Ti, Zr, Hf, Y, Th, U, Zn, Cd, B, Al, Ti, Si, Sn, Pb, P, Sb, Bi, Mg, Ca, Sr, Ba, Ga, V, and Sc. Also, in some embodiments, the reforming catalyst may include at least one rare earth element selected from the group consisting of La, Ce, Pr, Nd, Pm, Sm, Eu, Gd, Tb, Dy, Ho, Er, Tm, Yb, and Lu. Materials not normally considered to be catalytically active may also be employed as reforming catalysts, for example, refractory oxides such as cordierite, mullite, mullite aluminum titanate, zirconia spinels, and alumina. In yet another embodiment, the reforming catalyst may include metals selected from those having atomic number 21 to 29, 40 to 47 and 72 to 79, the metals Sc, Ti V, Cr, Mn, Fe, Co, Ni, Cu, Zr, Nb, Mo, Tc, Ru, Rh, Pd, Ag, Hf, Ta, W, Re, Os Ir, Pt, and Au.

The reforming reactor 204 may be operated over a wide range of pressures and temperatures. In some embodiments, the reforming reactor 204 may operate at pressure greater than atmospheric up to about 2,200 psi (15 MPa). In some embodiments, the reforming reactor 204 may be operated at a pressure in the range of from about 30 psi (205 KPa) to about 1,800 psi (12.4 MPa), more particularly from about 30 psi (205 KPa) to about 500 psi (3,450 KPa). In some embodiments, the feed mixture is contacted with the reforming catalyst at a temperature in excess of 1,110° F. (600° C.). Preferably, the feed mixture is contacted with the reforming catalyst at a temperature in the range of from about 1,110° F. (600° C.) to about 2,500° F. (1,370° C.). The feeds may be preheated prior to contacting the reforming catalyst. However, the scope of the disclosure is not limited to these pressures and temperatures for the reforming reactor 204. Rather, the reforming reactor 204 may have any suitable temperature and pressure for a particular application.

The Syngas stream 106 may be supplied from the reforming reactor 204 to the heat transfer zone 102. As illustrated, the heat transfer zone 102 may include a body 210 that contains the endothermic reaction zone 104. The body 210 may be in fluid communication with the reforming reactor 204. For example, the Syngas stream 106 may be supplied from the reforming reactor 204 to the body 210. In the illustrated embodiment, the endothermic reaction zone 104 may include tubes 212 disposed in the body 210. The tubes 212 may be at least partially disposed in the body 210. Endothermic reaction feed stream 108 may be supplied to the tubes 212 where the endothermic reaction feed stream 108 may be heated to a reaction temperature, for example, by heat transfer with the Syngas stream 106. The endothermic reactants in the endothermic reaction feed stream 108 may be allowed to react in the tubes 212 with endothermic reaction product stream 110 being withdrawn from the endothermic reaction zone 104. Suitable catalysts may also be disposed in the tubes 212, for example, depending on the particular endothermic reaction. As previously described, any suitable endothermic reaction may occur in the endothermic reaction zone, including, but not limited to, naphtha reforming, paraffin dehydrogenation, and steam cracking.

The Syngas stream 106 may be withdrawn from the heat transfer zone 102, for example, after exchanging heat with the endothermic reaction zone 104, and supplied to Syngas conversion unit 202. As illustrated, the Syngas stream 106 may be mixed with hydrogen stream 214 prior to the Syngas conversion unit 202. Alternatively, the Syngas stream 106 and the hydrogen stream 214 may be mixed in the Syngas conversion unit 202. In the Syngas conversion unit 202, any suitable technique may be used for conversion of the Syngas in the Syngas stream 106 to products, including, but not limited to, direction conversion of Syngas to olefins, aromatics, or combinations of olefins and aromatics. Examples of suitable products may include, but are not limited to, methanol, gasoline, dimethyl ether, distillates, lubricants, and BTX (e.g., mixtures of benzene, toulene, and xylenes). As illustrated, a product stream 216 may be withdrawn from the Syngas conversion unit 202. Additionally, carbon dioxide and water may also be produced in the Syngas conversion unit 202, depending, for example, on the particular conversion technique applied. In the illustrated embodiment, a carbon dioxide stream 218 and a water stream 220 may be withdrawn from the Syngas conversion unit 202.

Figure 3:
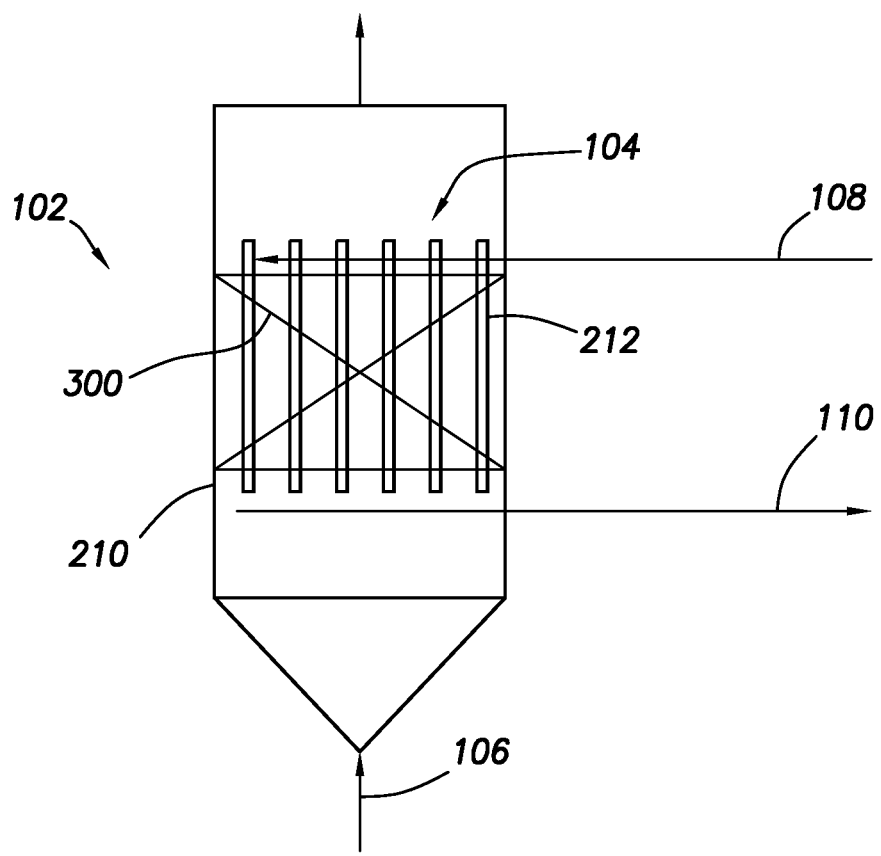
FIG. 3 is a schematic diagram illustrating another embodiment for heating an endothermic reaction feed stream.

FIG. 3 illustrates an embodiment of a heat transfer zone 102. As illustrated, the heat transfer zone 102 may include a body 210. In the illustrated embodiment, the heat transfer zone 102 may further include a fluidized bed 300 disposed in the body 210. The heat transfer zone 102 may also be disposed in the body 210. In the illustrated embodiment, the heat transfer zone 102 may include tubes 212 that may be disposed in the body 210. As illustrated, the tubes 212 may be disposed in the fluidized bed 300. The tubes 212 may be at least partially disposed in the fluidized bed 300. In some embodiments, the tubes 212 may be entirely disposed in the fluidized bed 300.

Fluidized bed 300 may include a fluidized bed of solid particles. The fluidized bed 300 may be heated by the Syngas stream 106. Tubes 212 may be heated by the fluidized bed 300 such that the endothermic reaction feed stream 108 in the tubes 212 may also be heated. As will be appreciated by those of ordinary skill in the art, the solid particles may be inert or catalytic. Examples of suitable inert particles may include, but are not limited to, fluid catalytic cracking spent catalyst, sand, silica and other powders having an average particle size ranging from about 10 microns about 100 microns, in some embodiments. In some embodiments, the solid particles may be catalytic. For example, the solid particles may catalyze the conversion of Syngas in the Syngas stream 106 to more valuable products. Examples of suitable catalysts for production of products from Syngas may include, but are not limited to, metal oxides or metal oxides on zeolites or silicoaluminophosphates (SAPO's). By way of further example, the solid particles may catalyze the conversion of a hydrocarbon-containing feed to Syngas in the heat transfer zone 102, with the Syngas being produced in the heat transfer zone 102 rather than in a separate unit. Examples of suitable catalysts for production of Syngas may include, but are not limited to, Nickel or other suitable metals containing solids. In some embodiments, the solid particles may be multi-functional such that a hydrocarbon-containing feed may be converted to valuable products in the heat transfer zone 102, with the Syngas being produced in the heat transfer zone 102 rather than in a separate unit. Examples of suitable multifunctional catalysts may include, but are not limited to, Cobalt or Manganese on a zeolite support, such as ZSM-5.

With continued reference to FIG. 3, an example method of operation of heat transfer zone 102 will now be described for transferring heat from production of Syngas to an endothermic reaction. As illustrated, the Syngas stream 106 may be supplied to heat transfer zone 102. In heat transfer zone 102, the Syngas stream 106 may heat the fluidized bed 300. For example, the fluidized bed 300 may be heated to temperatures ranging from about 50° F. (10° C.) to about 1,000° F. (540° C.) above the endothermic reaction temperature at pressures ranging from about 10 psi (70 KPa) to about 900 psi (6,200 KPa). More particularly, the fluidized bed 300 may be heated to temperatures ranging from about 50° F. (10° C.) to about 300° F. (150° C.) above the endothermic reaction temperature at pressures from about 10 psi (70 KPa) to about 200 psi (1,380 KPa). The fluidized bed 300 may heat the endothermic reaction zone 104. For example, the fluidized bed 300 may heat the tubes 212 disposed in the fluidized bed 300. The fluidized bed 300 may maintain a relatively constant temperature so that the heat transfer from the fluidized bed 300 may be considered isothermal. The tubes 212 may be supplied with the endothermic reaction feed stream 108, which may also be heated in the tubes 212 to a reaction temperature. The endothermic reactants in the endothermic reaction feed stream 108 may be allowed to react. An endothermic reaction product stream 110 may be withdrawn from the endothermic reaction zone 104 for further processing. The Syngas stream 106 may be withdrawn heat transfer zone 102 for further processing.

Figure 4:
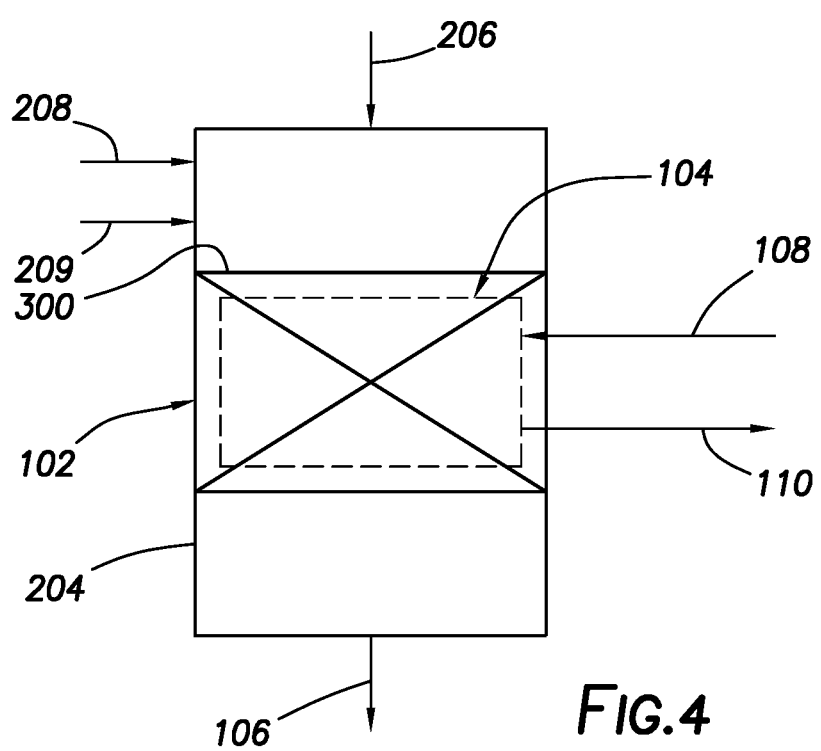
FIG. 4 is a schematic diagram illustrating yet another embodiment for heating an endothermic reaction feed stream.

FIG. 4 illustrates another embodiment of a heat transfer zone 102. As illustrated, the heat transfer zone 102 may disposed in a reforming reactor 204 for production of Syngas. For example, fluidized bed 300 may be disposed in the reforming reactor 204. In the illustrated embodiment, the heat transfer zone 102 and the endothermic reaction zone 104 may also be disposed in the reforming reactor 204. As illustrated, the endothermic reaction zone 104 may be disposed in the fluidized bed 300. In some embodiments, hydrocarbon-containing feed stream 206, oxygen stream 208, and steam stream 209 may be supplied to the reforming reactor 204. These streams may be separately provided to the reforming reactor 204, as illustrated, or one or more of the hydrocarbon-containing feed stream 206, oxygen stream 208, and steam stream 209 may be mixed prior to introduction into the reforming reactor 204. In the reforming reactor 204, hydrocarbon-containing feed in the hydrocarbon-containing feed stream 206 and the oxygen from the oxygen stream 208 may react to form Syngas. This reaction may be exothermic so heat may be generated to heat the fluidized bed 300. This heat may be transferred to the fluidized bed 300 from Syngas generated in the reforming reactor 204. As previously described, the fluidized bed 300 may be catalytic. In some embodiments, the fluidized bed 300 may catalyze the conversion of the hydrocarbon-containing feed to Syngas or the more valuable products, for example, where the fluidized bed 300 may be multi-functional. The fluidized bed 300 may heat the endothermic reaction zone 104 and, in turn, the endothermic reaction feed stream 108 supplied to the endothermic reaction zone 104. The endothermic reaction feed stream 108 may be heated to a reaction temperature. For example, the endothermic reaction feed stream 108 inside the tubes may be heated to temperature ranging from 900° F. (480° C.) to about 1750° F. (950° C.), more particularly, from 950° F. (510° C.) to about 1650° F. (900° C.). Pressures in the endothermic reaction zone 104 may range from about 10 psi (70 KPa) to about 600 psi (4,140 KPa), more particularly, from about 10 psi (70 KPa) to about 300 psi (2,070 KPa). The endothermic reactants in the endothermic reaction feed stream 108 may be allowed to react with an endothermic reaction product stream 110 being withdrawn from the endothermic reaction zone 104 for further processing. The Syngas stream 106 may be withdrawn from the heat transfer zone 102 for further processing.

While the invention has been described with respect to a number of embodiments and examples, those skilled in the art, having benefit of this disclosure, will appreciate that other embodiments can be devised which do not depart from the scope and spirit of the invention as disclosed herein. Although individual embodiments are discussed, the invention covers all combinations of all those embodiments.

While compositions, methods, and processes are described herein in terms of "comprising," "containing," "having," or "including" various components or steps, the compositions and methods can also "consist essentially of" or "consist of" the various components and steps. The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the invention, additionally, they do not exclude impurities and variances normally associated with the elements and materials used.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited.

The invention claimed is:

1. A method for providing heat to an endothermic reaction, comprising:
   producing Syngas in a reforming reactor comprising reacting a hydrocarbon-containing feed, steam, and oxygen in the reforming reactor to form the Syngas, and wherein the method of forming the Syngas further comprises:
      supplying a Syngas stream comprising the Syngas to the heat transfer zone, wherein the heat transfer zone comprises a fluidized bed and tubes disposed in the fluidized bed;
      heating the fluidized bed with the Syngas stream;
      supplying the endothermic reaction stream to the tubes disposed in the fluidized bed;
   heating the endothermic reaction stream with the fluidized bed, wherein the reactants in the endothermic reaction stream react in the tubes to form the endothermic reaction product stream
   recovering heat from the producing of the Syngas to heat an endothermic reaction stream in a heat transfer zone;
   allowing reactants in the endothermic reaction stream to react to form an endothermic reaction product stream; and
   withdrawing the endothermic reaction product stream from the heat transfer zone.

2. The method of claim 1, wherein the endothermic reaction is selected from the group consisting of steam cracking, naphtha reforming, and paraffin dehydrogenation.

3. The method of claim 1, wherein the heat transfer zone is disposed in the reforming reactor, wherein the heat transfer zone comprises a fluidized bed.

4. The method of claim 3, further comprising supplying the endothermic reaction stream to tubes disposed in the fluidized bed.

5. The method of claim 3, wherein the fluidized bed is catalytic.

6. The method of claim 1, wherein the recovering the heat comprises supplying a Syngas stream comprising the Syngas to the heat transfer zone.

7. The method of claim 6, wherein the recovering the heat comprises heating a fluidized bed with the Syngas stream.

8. The method of claim 7, wherein the fluidized bed is catalytic and catalyzes conversion of the Syngas in the Syngas stream to a product.

9. The method of claim 6, wherein the Syngas stream is supplied to the heat transfer zone at a temperature ranging from about 1,400° F. to about 2,500° F. and a pressure ranging from about 5 pounds per square inch to about 900 pounds per square inch.

10. The method of claim 1, wherein the endothermic reaction stream is heated to a temperature ranging from about 900° F. to about 1,750° F. at a pressure ranging from about 1 pounds per square inch to about 150 pounds per square inch.

11. The method of claim 1, wherein the endothermic reaction stream is supplied to an endothermic reaction zone in the heat transfer zone at a temperature within about 300° F. of a reaction temperature.

12. The method of claim 1, wherein the allowing reactants in the endothermic reaction stream to react comprises reacting a hydrocarbon feedstock in presence of steam to form olefins.

13. The method of claim 1, further comprising converting the Syngas to a product, wherein the product comprises at least one product selected from the group consisting of methanol, dimethyl ether, gasoline, distillate, mixtures of butylene, toluene, and xylenes, and combinations thereof.

14. A method for reducing flue gas emissions from furnaces of endothermic reactions, comprising:
   supplying an endothermic reaction stream to an endothermic reaction zone;
   recovering heat from a Syngas in the endothermic reaction zone to heat the endothermic reaction stream; and
   allowing reactants in the endothermic reaction stream to react to form an endothermic reaction product stream;
   wherein the Syngas recovered from the endothermic reaction zone comprises reacting a hydrocarbon-containing feed, steam, and oxygen in the endothermic reaction zone to form the Syngas, and wherein the method of forming the Syngas further comprises:
      supplying a Syngas stream comprising the Syngas to the endothermic reaction zone, wherein the endothermic reaction zone comprises a heat transfer zone comprising a fluidized bed and tubes disposed in the fluidized bed;
      heating the fluidized bed with the Syngas stream; and
      supplying the endothermic reaction stream to the tubes disposed in the fluidized bed.

15. The method of claim 14, further comprising converting the Syngas to a product, wherein the product comprises at least one product selected from the group consisting of methanol, dimethyl ether, gasoline, distillate, mixtures of butylene, toluene, and xylenes, and combinations thereof.

* * * * *